(12) United States Patent
Elgort et al.

(10) Patent No.: US 8,611,982 B2
(45) Date of Patent: Dec. 17, 2013

(54) ACTIVE DEVICE TRACKING USING LIGHT WITH ORBITAL ANGULAR MOMENTUM TO HYPERPOLARIZED MRI

(75) Inventors: Daniel R. Elgort, New York, NY (US); Lucian Remus Albu, Forest Hills, NY (US)

(73) Assignee: Koninklijke Philips N.V., Eindhoven (NL)

(*) Notice: Subject to any disclaimer, the term of this patent is extended or adjusted under 35 U.S.C. 154(b) by 82 days.

(21) Appl. No.: 13/131,881

(22) PCT Filed: Nov. 5, 2009

(86) PCT No.: PCT/IB2009/054924
§ 371 (c)(1),
(2), (4) Date: May 31, 2011

(87) PCT Pub. No.: WO2010/064155
PCT Pub. Date: Jun. 10, 2010

(65) Prior Publication Data
US 2011/0230757 A1    Sep. 22, 2011

Related U.S. Application Data

(60) Provisional application No. 61/120,180, filed on Dec. 5, 2008.

(51) Int. Cl.
*G01V 3/00* (2006.01)

(52) U.S. Cl.
USPC ................... 600/423; 600/420; 324/307

(58) Field of Classification Search
USPC ................... 600/410, 420, 423; 324/307
See application file for complete search history.

(56) References Cited

U.S. PATENT DOCUMENTS 6,818,202 B2    11/2004 Pines et al.

2006/0173283 A1    8/2006 Axelsson et al.
2008/0116890 A1    5/2008 Hurd

FOREIGN PATENT DOCUMENTS

| WO | 2009081360 A1 | 7/2009 |
| WO | 2009090610 A1 | 7/2009 |
| WO | WO2009081360 A1 | 7/2009 |

OTHER PUBLICATIONS

Magnussun, et al. "Passive Catheter Tracking During Interventional MRI Using Hyperpolarized C-13", Magnetic Resonance in Medicine, V. 57, Issue 6, pp. 1140-1147 (Jun. 2007).
Allen, et al. The Orbital Angular Momentum of Light, E. Wolf, Progress in Optics XXXIX, 1999 Elsevier Science B.V., pp. 291-372.
Buckingham, et al. "The Effect of Circularly Polarized Light on NMR Spectra", Molecular Physics, 1997, vol. 91, No. 5, 805-813.
Elgort, et al. "Direct Optical Hyperpolarization of Liquids", Proc. Intl. Soc. Mag. Reson. Med. 16 (2008), pp. 3200.

(Continued)

*Primary Examiner* — Michael Rozanski

(57) ABSTRACT

One or more light beam endowed with photonic orbital angular momentum generating devices are mounted at preselected locations on an insertable instrument to hyperpolarize nuclear magnetic dipoles in a region of interest. The hyperpolarized nuclear magnetic dipoles are caused to resonate, generating magnetic resonance signals. A controller controls gradient coils to induce a magnetic field gradient across the region of interest, such that the frequency of the resonance signals is indicative of spatial positions. A frequency-to-position decoder converts the resonance signal frequencies into spatial positions. A video processor combines the spatial positions and a portion of a diagnostic image from a diagnostic image memory into a combined image which depicts the location of the region of interest or a portion of the instrument marked on the diagnostic image and displays the combined image on a monitor.

15 Claims, 2 Drawing Sheets

(56) References Cited

OTHER PUBLICATIONS

Romero, L.C. Davila et al. "A quantum electrodynamics framework for the nonlinear optics of twisted beams", Journal of Optics B: Quantum and Semiclassical Optics, 4, S66, 2002.

Courtial, J. et al. "Gaussian beams with very high orbital angular momentum", Optics Communications 144 (1997) 210-213.

Babiker, M. et al. "Orbital Angular Momentum Exchange in the Interaction of Twisted Light with Molecules", PRL, vol. 89, No. 14, Sep. 30, 2002.

ACTIVE DEVICE TRACKING USING LIGHT WITH ORBITAL ANGULAR MOMENTUM TO HYPERPOLARIZED MRI

This application is a national stage application under 35 U.S.C. §371 of international Application No. PCT/IB2009/054924 filed on Nov. 5, 2009, which claims priority to U.S. Provisional Application No. 61/120,180, filed on Dec. 5, 2008.

The present application relates to the tracking arts. It finds particular application with image guided, minimally invasive surgical procedures and will be described with particular reference thereto. However, it will also find application in conjunction with the location of other instrumented objects.

When performing minimally invasive image guided surgery, the surgical region and the working end of the surgical instrument is typically not visible to the surgeon. Rather, the surgeon "sees" the surgical region via diagnostic images. In order for these minimally invasive surgical systems to function as intended, the surgeon needs to know where the working end of the surgical instrument is relative to the target tissue(s) in the surgical region area of the patient and the diagnostic image.

Mechanical tracking systems rigidly affix surgical tools to a static reference plane, such as the operating table. A series of instrumented joints between the static frame of reference plane and the tool allow the tool to be manipulated. This approach is appropriate only for rigid tools and often has a significantly restricted range of motion/ergonomics.

Some tracking techniques measure the working end or tip of the instrument indirectly. That is, when using a rigid tool, such as a biopsy needle, tracking elements are placed on the visible end of the instrument, e.g., light or other energy emitters or reflectors. Light from the emitters is tracked by video cameras or the like. By electronically calculating the position of the light emitters and by knowing the geometric relationship between the light emitters and the tip of the instrument, the location of the tip can be mathematically calculated. These indirect methods have drawbacks such as inaccuracy if the instrument is not rigid, if the surgeon or other equipment in the room blocks the line of sight between the light emitter and the electronic system, and the like.

Other techniques have been developed which locate the working end or tip of the instrument directly in three dimensions. For example, the tip of the instrument can be imaged with x-ray fluoroscopic or CT techniques. However, these radiation-based techniques subject the patient, and, to a lesser extent, the medical personnel in the room to a significant amount of radiation.

In another technique, the tip or other portions of the instrument are configured such that they show up in a magnetic resonance image. This enables additional diagnostic images to be generated periodically to monitor movement of the instrument. This technique tends to be relatively slow and requires the surgical site to be in the bore or imaging region of an MRI scanner.

In another technique, an active antenna is disposed adjacent the tip. This antenna is used to measure applied magnetic resonance imaging signals from which it generates coordinates of the antenna in three dimensions in the coordinate system of the MRI scanner. This requires wires from the antenna that run the length of the instrument to external circuitry, which are subject to heating under the fields applied during magnetic resonance imaging. Moreover, this technique suffers from inaccuracy in the vicinity of metal objects which distort the fields, and in the presence of the highly magnetic environment found inside an MRI scanner.

The present application contemplates a new and improved tracking technique which overcomes the above-referenced problems and others.

In accordance with one aspect, a tracking system for an insertable instrument is provided. At least one light beam endowed with orbital angular momentum generating device is configured to be mounted to a selected location on the insertable instrument to hyperpolarize nuclear magnetic dipoles in a region of interest adjacent thereto. An RF coil receives resonance signals from the nuclear magnetic dipoles in the region of interest. A controller controls gradient coils for inducing a magnetic field gradient across the region of interest to encode spatial position in a frequency of the resonance signals. A radio frequency receiver receives the resonance signals from the RF coil and a frequency-to-position decoder converts the received nuclear magnetic resonance signals into corresponding spatial positions. An image memory stores a diagnostic image of a subject into which the insertable instrument is to be inserted. Optionally, a video processor combines the spatial position from the frequency-to-position decoder and at least a portion of the diagnostic image from the diagnostic image memory into a combined display with the location of the region of interest or a portion of the instrument marked on the diagnostic image and controls the display of the combined image on a monitor.

In accordance with another aspect, a method of tracking an insertable instrument is provided. With the instrument inserted into a subject, nuclear magnetic dipoles are polarized in a region of interest at a preselected location along the instrument using light beams endowed with orbital angular momentum. A magnetic resonance sequence is applied which identifies locations of the polarized nuclear magnetic dipoles.

In one embodiment, the OAM hyperpolarized nuclear spins are polarized in at any orientation relative to a $B_0$, which represents a constant uniform magnetic field such as the one produced by the bore of an MRI instrument; this approach enables standard MR-localization pulse sequences, using non-selective or thick slab excitations, to be used to detect the polarized nuclear spins and localize the device. Detection of the device is possible because the hyperpolarized nuclear spins resonance response have an increased signal intensity relative to the background signal which contains nuclear spins that are weakly polarized by the MR system's $B_0$ magnetic field.

One advantage resides in improved accuracy in tracking the working end or tip of surgical instruments.

Another advantage resides in the generation of tip location information substantially in real time during a surgical procedure.

Another advantage resides in freedom from or at least minimal interference with movement of the surgeon and other instruments around the patient during surgery.

Still further advantages and benefits will become apparent to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
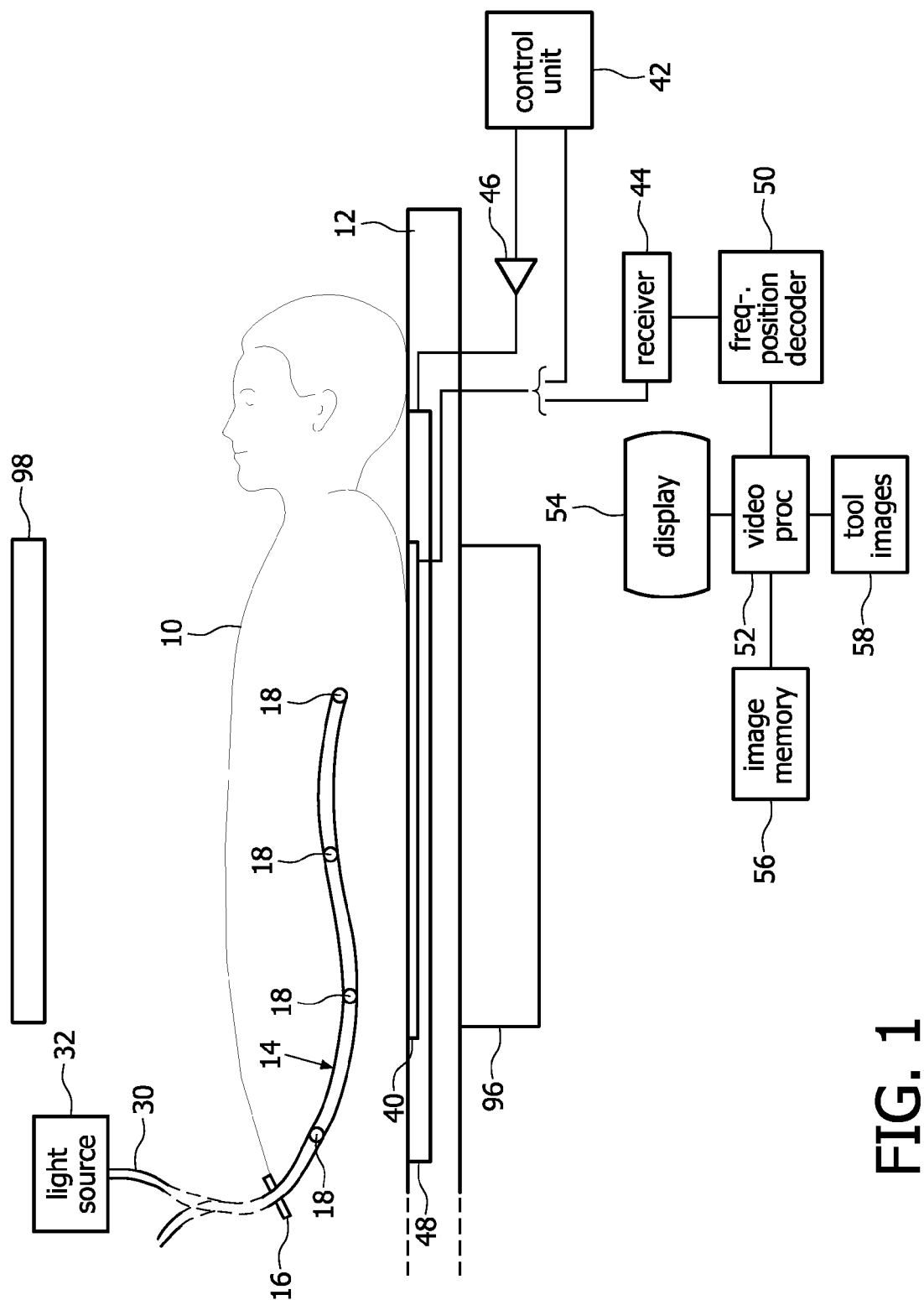
FIG. 1 is a diagrammatic illustration of a patient, an insertable instrument, and tracking system.

With reference to FIG. 1, a patient 10 is disposed on a support surface 12 in preparation for a minimally invasive surgical procedure. A minimally invasive surgical device such as a catheter 14 is inserted into the patient through a port 16, e.g., in the femoral artery. A light beam endowed with orbital angular momentum generation device 18 is disposed at one or more known locations along the catheter, e.g., adjacent the tip. By way of example, a balloon catheter is typically inserted through the port 16 and fed along the patient's arterial system to the location of the blockage, when inserting a stent or performing balloon angioplasty. As the catheter moves through the arterial system, it is tracked to mark its location. Guide wires or other navigational systems are used to direct the tip of the catheter to follow the appropriate branches to use the arterial system analogous to a highway system to bring the tip to the location of the blockage.

Figure 2:
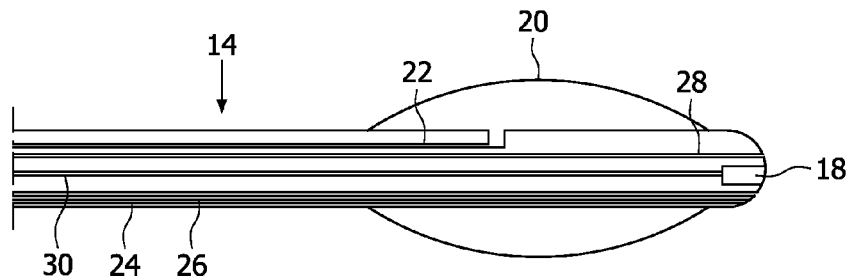
FIG. 2 is a diagrammatic illustration of an exemplary working end of an instrument instrumented with a light beam endowed with orbital angular momentum tracking system.

With continuing reference to FIG. 1 and further reference to FIG. 2, the catheter 14 is a balloon catheter connected with a balloon 20 (illustrated inflated), connected with an air channel 22, for selectively inflating it. A guide wire passage 24 receives a guide wire 26 for causing the tip of the catheter to turn in a selected direction. A channel 28 terminates in a port for releasing imaging contrast agents, medications, and the like into the blood adjacent the tip of the catheter.

The light beam endowed with orbital angular momentum generator 18 is connected to an optic fiber 30 which extends through the catheter. The optic fiber 30 extends from a light source 32 external to the patient to the light beam endowed with orbital angular momentum generating device 18. The light beam endowed with orbital angular momentum generating device 18 uses light endowed with orbital angular momentum to hyperpolarize nuclear magnetic dipoles, such as protons or hydrogen magnetic dipoles in blood or other body tissues adjacent the tip. The hyperpolarization occurs in a very limited location, but is 1,000-1,000,000 times greater than the polarization achieved with today's commercial magnetic resonance imaging systems. The polarized nuclear magnetic dipoles can be caused to resonate at a frequency that is proportional to the strength of a surrounding magnetic field. Using magnetic field gradients analogous to an MRI imaging system, the frequency with which these dipoles resonate can be positionally encoded.

With continuing reference to FIG. 1, an RF coil 40 is disposed adjacent the patient. In the embodiment of FIG. 1, the RF coil is embedded into the patient support 12 adjacent its upper surface. However, the RF coil can be positioned in other locations, such as on the surface of the patient, above the patient, or the like. A control unit 42 controls either the RF coil 40 or the light beam endowed with orbital angular momentum generating device to induce nuclear magnetic resonance in the hyperpolarized nuclear magnetic dipoles. The resonating dipoles generate a magnetic resonance signal of a characteristic frequency which is received and demodulated by a receiver 44.

The controller 42 further controls a gradient magnetic field generating system in which a gradient coil power supply 46 supplies pulses of power to gradient coils 48. In the illustrated embodiment, the gradient coils 48 include x, y, and z-gradient coils for inducing magnetic field gradients in each of three orthogonal directions. Planar gradient coils may be of the construction commonly used in open MRI systems. The resonance frequency of the resonance signal varies in accordance with the strength of the magnetic field. Thus, when the gradient magnetic field is applied, the frequency of the received resonance signal is indicative of its spatial position. For example, the controller causes the gradient power supply 46 to cause the x-gradient coil to apply an x-gradient and the receiver receives the magnetic resonance signal. From the frequency of the x-gradient signal, a frequency to position decoder 50 determines the position of the light beam endowed with orbital angular momentum generating device 18 in the spatial coordinate system of the gradient coils, hence the patient support 12. This process is repeated to obtain the spatial position in the y- and z-directions. Although a linear gradient magnetic field simplifies the frequency to spatial position calculation, other gradient shapes can also be used.

Video processor 52 controls a display device 54 to display a diagnostic image of the patient from an image memory 56. The diagnostic image is aligned with the coordinate system of the patient support and the patient using any of a variety of known techniques. Typically, the diagnostic image is a three-dimensional image and the surgeon displays one or more selected slices. The selected slices typically change such that at least one displayed slice includes the plane in which the orbital angular momentum generation device 18 lies. Because the diagnostic image is spatially aligned or coordinated with the patient support 12, the x-, y-, and z-positional information from the frequency to position decoder 50 is used by the video processor 52 to identify the voxel of the diagnostic image corresponding to the position of the orbital angular momentum generating device, the tip of the instrument, or other point on the instrument that is positioned with a known offset from the angular momentum generating device. In one embodiment, the position of the focal point of the light beam endowed with orbital angular momentum generating device is displayed as a bright spot, cross hairs, or other symbol on one or more of the displayed diagnostic images. Alternately, a diagnostic tool image generator 58 generates an image representation of the catheter or other inserted device or a portion thereof for superimposition on the diagnostic image.

Figure 3:
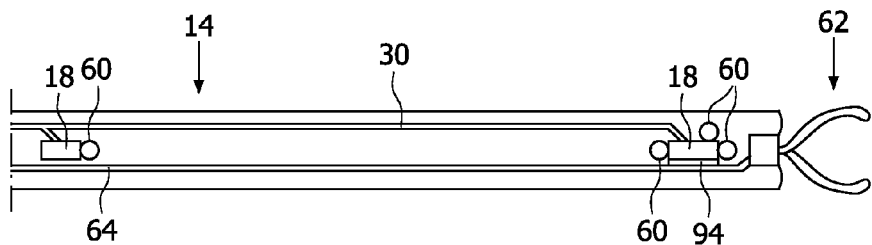
FIG. 3 is an alternate embodiment of an instrument with a light beam endowed with orbital angular momentum tracking system.

With reference to FIG. 3, one or more light beam endowed with angular momentum generators 18 are disposed along the insertable instrument. Each light beam endowed with orbital anular momentum generator is again connected with a light source via an optical fiber 30. Each light beam endowed with orbital angular momentum generator 18 generates light beam endowed with orbital angular momentum which it uses to hyperpolarize the magnetic dipoles of the nuclei in one or more samples 60. In one example, the samples are small, hollow beads which contain a hyperpolarizable substance. In one embodiment the hyperpolarizable substance is a noble gas like xenon or helium. In another embodiment, the hyperpolarizable material is a liquid, such as water or an oil. By positioning two samples along an axis of the inserted instrument, the trajectory of the instrument can be determined. By positioning a third sample which s non-collinear with the first two, a rotational orientation of the insertable device can be determined. By positioning hyperpolarized samples along the length of the device, the path which the inserted instrument is following can be illustrated in the displayed diagnostic image. An end effector 62 is controlled via a control line or channel 64, e.g., a pneumatic system.

Figure 4:
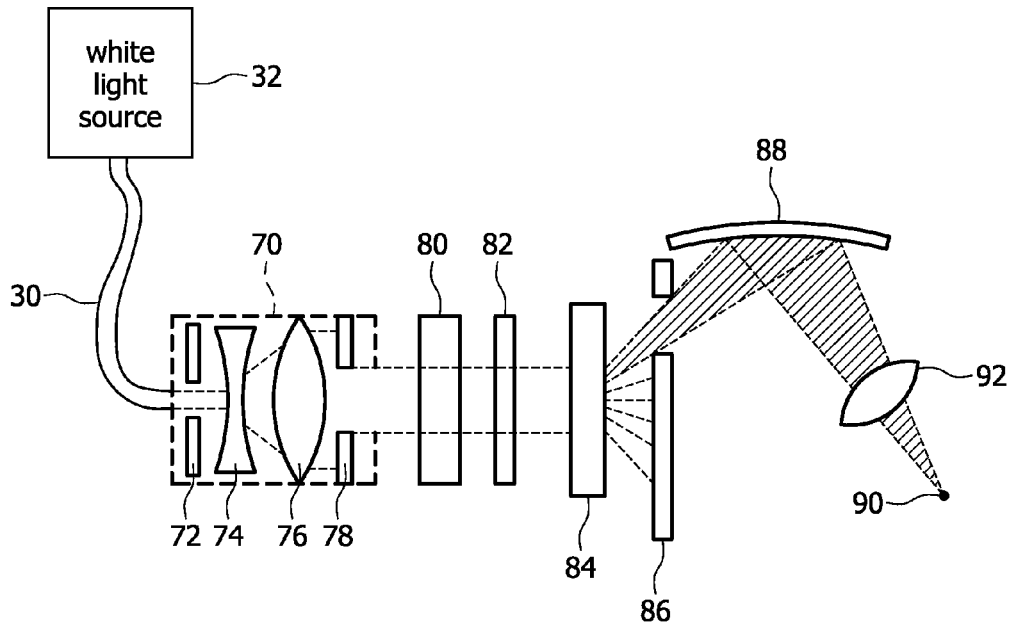
FIG. 4 illustrates details of an exemplary light beam endowed with orbital angular momentum generating system for generating hyperpolarized nuclear magnetic dipoles.

With reference to FIG. 4, the light beam endowed with orbital angular momentum generating device 18 includes an arrangement of optical elements, preferably disposed on a small chip or microchip sized to be accommodated in the inserted instrument. In the balloon catheter example, balloon catheters (with the balloon not inflated) are commonly about 2-5 mm in diameter. Further, although the electromagnetic radiation which is to be endowed with orbital angular momentum is described as visible monochromatic or multichromatic (e.g. white) light, other types of electromagnetic radiation are also contemplated. Visible light interacts with hydrogen atoms an other atoms or molecules of interest and has no damaging effect on living tissue. More specifically, visible light indirectly creates a magnetic dipole polarization in the protons via its interactions with the electron orbitals and the angular momentum of the molecule. There are other frequencies of electromagnetic radiation which enable the protons to be interacted with directly. Electromagnetic radiation or light above r below the visible spectrum is also contemplated. Modifying the frequency content of the light and/or the amount of orbital angular momentum in the light beam molecules to be more strongly polarized and enables specific molecules to be selectively polarized. The beam of light carried by the optical fiber or other waveguide 30 is expanded by a beam expander 70. The beam expander includes an entrance collimator 72 for collimating the light or electromagnetic radiation into narrow beam. A concave lens 74 diverges the light beam which is refocused by a focusing lens 76. The intensity non uniformity of the light beam is rejected with an exit collimator 78. in one embodiment, the exit collimator narrows the beam to about 1 mm.

A linear polarizer 80 and quarter wave plate 82 circularly polarize the light. The linear polarizer gives the unpolarized light a single linear polarization and the quarter wave plate shifts the linearly polarized light by a quarter wavelength, circularly polarizing it. Using circularly polarized light is not essential, but has the added advantage of polarizing the spin states of electrons.

The circularly polarized light is passed through a phase pattern or phase hologram 84 which imparts orbital angular momentum to the light beam. The order l of the orbital angular momentum is dependent on the phase hologram 84. In one embodiment, a value of l=40 is imparted to incident light, although higher values of l are also contemplated. Alternately, the phase pattern or hologram 84 may be embodied in other optics, such as combinations of cylindrical lenses, wave plates, fixed phase holograms in glass or plastic, or the like.

Not all the light passing through the holographic plate 84 is imparted with orbital angular momentum. Generally, when electromagnetic waves interact with the phase hologram, they are diffracted into a diffraction pattern. The middle represents the $0^{th}$ order diffraction which, in this case, is light with no orbital angular momentum. Patterns adjacent to this center component represent diffracted beams of different orders that are composed of photons beams carrying orbital angular momentum.

A spatial filter 86 is placed after the holographic plate to selectively pass only light with the desired orbital angular momentum through an aperture and blocks all other diffracted components of light. That is, the spatial filter 86 passes light having orbital angular momentum of only one value. The light passed by the spatial filter 86 is collected using concave mirror(s) 88 and focused on the region of interest 90 with a convergent lens 92. The light endowed with orbital angular momentum is advantageously focused on the region of interest within a image size as close as possible to the size of the Airy disk associated to the light carrying the same Gaussian beam frequency. Again, the region of interest can either be tissue adjacent the inserted instrument or a liquid or gas sample that is incorporated into the device 60.

Rather than using only the light with orbital angular momentum to polarize the nuclear magnetic dipoles of interest, the light can be used to supplement a magnetic field. The magnetic field can be the $B_0$ magnetic field of a magnetic resonance imaging system, or a magnetic field supplied by the tracking system. In one example, a permanent magnet 94 is positioned adjacent the target dipoles and appropriately oriented to generate a steady state magnetic field through the region of interest in which nuclear magnetic resonance is to be induced. In another embodiment, a magnet 96 is disposed below the patient support 12 to generate a vertical $B_0$ field through the region of interest. Optionally, a pole piece of opposite polarity or a flux focusing structure 98 can be disposed above the subject, e.g., on the ceiling of the operating room, or the like. In another alternate embodiment, the gradient and radio frequency coils are the gradient and radio frequency coils of an open or other magnetic resonance imaging system.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference numerals in the claims are for illustration purposes only and do not limit their protective scope; and
d) several "means" may be represented by the same item or hardware or software implemented structure or function.

The invention claimed is:

1. A tracking system for an insertable instrument comprising:
at least one photonic orbital angular momentum generating device configured to be mounted to a selected location on the insertable instrument to hyperpolarize nuclear magnetic dipoles in a region of interest adjacent thereto;
an RF coil configured to receive nuclear magnetic resonance signals from the nuclear magnetic dipoles in the region of interest;
a controller configured to control gradient coils for inducing a magnetic field gradient across the region of interest, the gradient magnetic field encoding spatial positions in a frequency of the nuclear magnetic resonance signals;
a radio frequency receiver configured to receive the nuclear magnetic resonance signals from the RF coil;
a frequency-to-position decoder configured to convert the received nuclear magnetic resonance signals into corresponding spatial positions;
an image memory configured to store a diagnostic image of a subject into which the insertable instrument is to be inserted; and
a video processor configured to combine the spatial positions from the frequency-to-position decoder and at least a portion of the diagnostic image from the image memory into a combined image with the location of the region of interest and a portion of the instrument marked on the diagnostic image and configured to control the display of the combined image on a monitor.

2. The tracking system according to claim 1, wherein the photonic orbital angular momentum generating device is further configured to generate from received electromagnetic radiation a light endowed with an orbital angular momentum to polarize nuclear spins and nuclear magnetic dipoles in a sample disposed in the region of interest using the interaction of the light endowed with the orbital angular momentum with molecular angular momentum, molecular orbitals, electron spin states and nuclei spin states.

3. The tracking system according to claim 1, further including a waveguide for conveying electromagnetic radiation from external to the subject through the insertable instrument to the photonic orbital angular momentum generating device.

4. The tracking system according to claim 1, further including:
a patient support configured to support the subject; and
wherein the patient support includes at least on of the RF coil and the gradient coils, the at least one of the RF coil an the gradient coils being embedded in the patient support so as not to interfere with a surgeon during a surgical procedure.

5. The tracking system according to claim 1, further including:
a magnet positioned to generate a static magnetic field through the region of interest.

6. The tracking system according to claim 1, further including:
a permanent magnet configured to be mounted in the insertable instrument adjacent the region of interest.

7. The tracking system according to claim 1, further including:
a sample in the region of interest, the photonic orbital angular momentum device hyperpolarizing nuclear spins in the sample.

8. The tracking system according to claim 1,
wherein the video processor is further configured to generate a depiction of at least a portion of the instrument based on a plurality of resonating regions of interest for display superimposed on the displayed combined image, and wherein the plurality of resonating regions of interest include nuclear spins that resonate, each of the plurality of resonating regions of interest being at a preselected position relative to the instrument.

9. A method of tracking an insertable instrument the method comprising the acts of:
with the instrument inserted into a subject, polarizing nuclear magnetic dipoles in a region of interest at a preselected location along the instrument by imparting an orbital angular momentum to nuclear spins of the magnetic dipoles; and
applying a magnetic resonance sequence to generate nuclear magnetic resonance signals for identifying locations of the polarized nuclear magnetic dipoles;
controlling gradient coils for inducing a magnetic field gradient across the region of interest, the gradient magnetic field encoding spatial positions of the region of interest in a frequency of the nuclear magnetic resonance signals;
receiving the nuclear magnetic resonance signals by a radio frequency receiver;
converting the received nuclear magnetic resonance signals by a freguency-to-position decoder into corresponding spatial positions;
storing in an image memory a diagnostic image of the subject into which the insertable instrument is to be inserted;
combining the spatial positions from the frequency-to-position decoder and at least a portion of the diagnostic image from the image memory into combined image with the location of the region of interest and a portion of the instrument marked on the diagnostic image; and
displaying the combined image on a monitor, the combined image including the spatial positions of the region of interest superimposed on the diagnostic image.

10. The method according to claim 9, wherein the polarizing act includes hyperpolarizing the nuclear spins in any orientation relative to a static magnetic field.

11. The method according to claim 10, wherein the polarizing act further includes the acts of:
conveying light from a light source exterior to the subject through the insertable instrument to a light beam endowed with an orbital angular momentum generating device;
with the light beam endowed with the orbital angular momentum generating device, converting received light into light having the orbital angular momentum, wherein the orbital angular momentum has a single value; and
directing the light endowed with the orbital angular momentum on the region of interest to polarize the nuclear magnetic dipoles.

12. The method according to claim 11, wherein the directing act includes focusing the light endowed with the orbital angular momentum on the region of interest within an image size taking into account the size of an Airy disk associated to the light beam carrying a same Gaussian beam frequency as the light endowed with the orbital angular momentum.

13. The method according to claim 11 wherein the hyperpolarized nuclear magnetic dipoles are in a plurality of samples fixedly mounted to one or more light beams endowed with orbital angular momentum generation devices, the samples being disposed at each of a plurality of preselected locations along the insertable instrument, the method further including the acts of:
determining a spatial position of each of a plurality samples; and
displaying the spatial position of each of the samples and a depiction of a portion of the instrument derived from the plurality of sample positions superimposed on the diagnostic image of the subject.

14. The method according to claim 9, further including the act of:
moving the insertable instrument through the subject; and
repeatedly determining a spatial position of the region of interest to track the region of interest as the insertable instrument moves through the subject.

15. The method according to claim 14, wherein the insertable instrument is a non-rigid instrument and the method further comprises the act of:
steering a working end of the insertable instrument in accordance with the diagnostic image such that the region of interest and the working end of the insertable instrument follows a selected trajectory through the subject.

* * * * *